(12) United States Patent
Trantow et al.

(10) Patent No.: US 6,563,307 B2
(45) Date of Patent: May 13, 2003

(54) EDDY CURRENT INSPECTION PROBE (75) Inventors: Richard Lloyd Trantow, Depoe Bay, OR (US); Francis Howard Little, Cincinnati, OH (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 09/921,807

(22) Filed: Aug. 3, 2001

(65) Prior Publication Data
US 2003/0025496 A1 Feb. 6, 2003

(51) Int. Cl.[7] .......................... G01N 27/72; G01N 27/82
(52) U.S. Cl. ......................... 324/219; 324/238
(58) Field of Search ................ 324/219, 238, 324/220, 236, 237, 239, 240, 241, 242, 243, 262; 73/622, 623

(56) References Cited

U.S. PATENT DOCUMENTS 5,315,234 A  5/1994 Sutton, Jr. et al.
5,442,286 A  8/1995 Sutton, Jr. et al.
5,903,147 A  * 5/1999 Granger, Jr. et al. ........ 324/219
6,339,326 B1 * 1/2001 Trantow ................... 324/219

* cited by examiner

Primary Examiner—Edward Lefkowitz
Assistant Examiner—Subhash Zaveri
(74) Attorney, Agent, or Firm—V. G. Ramaswamy; Sonnenschein Nath & Rosenthal (57) ABSTRACT An eddy current inspection probe for inspecting a preselected surface. The eddy current inspection probe includes an expandable element at least partially defining an interior space which is expandable by introducing a pressurized fluid into the interior space from a collapsed position to an expanded position for contacting the preselected surface of the component for inspecting the surface. The probe also includes an eddy current array positioned over the expandable element for generating and detecting magnetic fields in the component to inspect the preselected surface.

15 Claims, 9 Drawing Sheets

EDDY CURRENT INSPECTION PROBE

BACKGROUND OF THE INVENTION

The present invention relates generally to eddy current inspection probes for inspecting a surface of a manufactured component, and more particularly to a probe having an improved fit with the surface of the component.

Eddy current inspection is commonly used to detect flaws in surfaces of manufactured components such as gas turbine engine components. During this type of inspection, electromagnetic induction is used to induce eddy currents in the component being inspected. An array of coils inside an eddy current probe generates alternating magnetic fields which induce the eddy currents in the component when the probe is moved near the component. When flaws are present in the component, the flow of eddy currents is altered. The altered eddy currents produce changes in a secondary magnetic field which are detected by the array of coils inside the eddy current probe. The array generates an electrical signal in response to the altered secondary magnetic field. The amplitude of the electrical signal is generally proportionate to the size of the flaw. Thus, approximate sizes and general locations of flaws may be determined using eddy current probes.

The array must be kept at a constant distance from the surface of the component being inspected to ensure the amplitude of the electrical signal is proportionate to flaw size. One way of ensuring a constant distance is by sizing and shaping the probe substantially identically to the feature being inspected. For instance, if the surface of an opening in a gas turbine engine disk such as a dovetail slot bottom is being inspected, a probe sized and shaped substantially identically to the opening is used.

Frequently, the probe is made to compress or collapse so it can fit into the opening. These collapsible probes generally have a compressible or collapsible core inside a flexible covering which holds the array. In the past, gaps sometimes occurred between the probe and the surface which also prevented the array from being positioned at a uniform distance from the surface being inspected due to variations in size and shape of the actual features being inspected.

SUMMARY OF THE INVENTION

Among the several features of the present invention may be noted the provision of an eddy current inspection probe for inspecting a preselected surface at least partially defining an opening in a component. The eddy current inspection probe comprises an expandable element at least partially defining an interior space which is expandable by introducing a pressurized fluid into the interior space from a collapsed position for inserting the probe into and removing the probe from the opening in the component to an expanded position in which the probe is sized and shaped for at least partially filling the opening and for contacting the preselected surface of the component for inspecting the surface. Further, the probe includes an eddy current array positioned over the expandable element for generating and detecting magnetic fields in the component to inspect the preselected surface of the component. The eddy current array has an outer surface shaped substantially identically to the preselected surface of the component when the expandable element is in the expanded position for maintaining the outer surface of the array at a preselected distance from the surface of the component.

Other features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
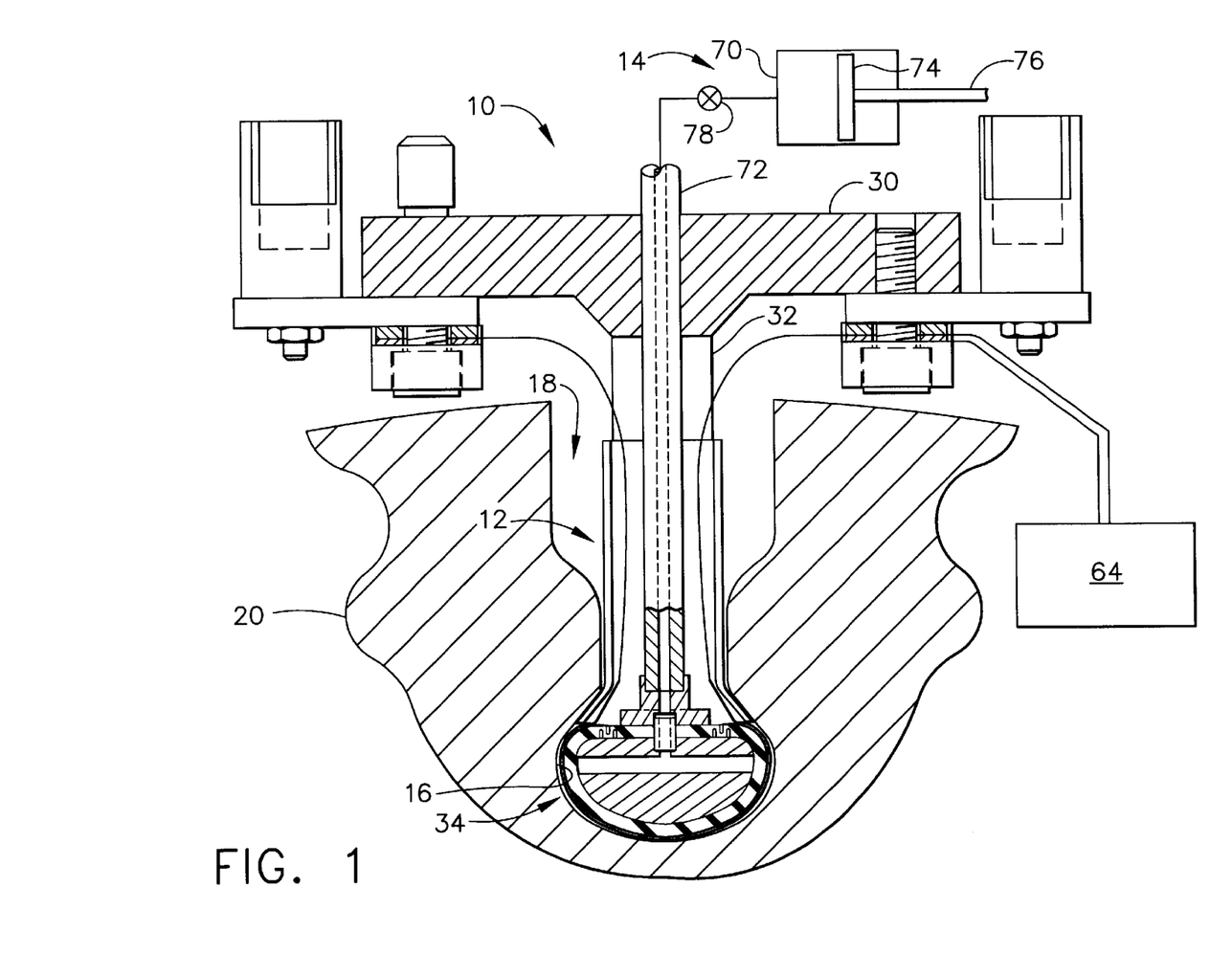
FIG. 1 is a vertical cross section of an eddy current inspection system of a first embodiment of the present invention shown in an opening of a component.

Referring now to the drawings and in particular to FIG. 1, an eddy current inspection system of the present invention is designated in its entirety by the reference number 10. The system 10 includes a probe (generally designated by 12) and a fluid delivery system (generally designated by 14). The probe 12 is sized and shaped for inspecting a preselected surface 16 (e.g., a dovetail slot bottom of a gas turbine engine disk) at least partially defining an opening, generally designated by 18, in a component 20 (partially shown in FIG. 1). The probe 12 is mounted on a conventional fixture (not shown) positioned adjacent the component 20 to be inspected.

Figure 2:
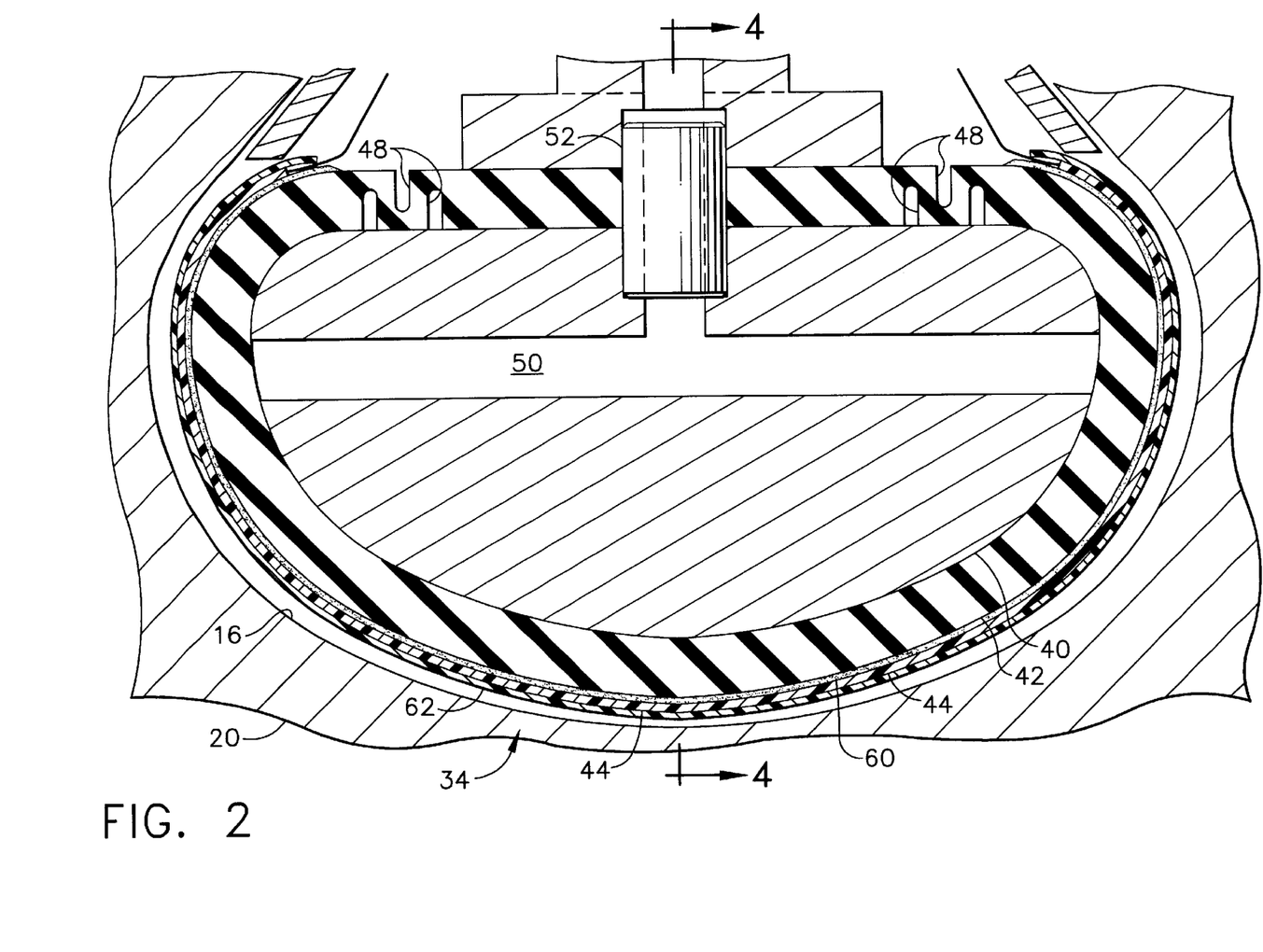
FIG. 2 is a detail of a probe of the system and component showing the probe in a collapsed position.
Figure 3:
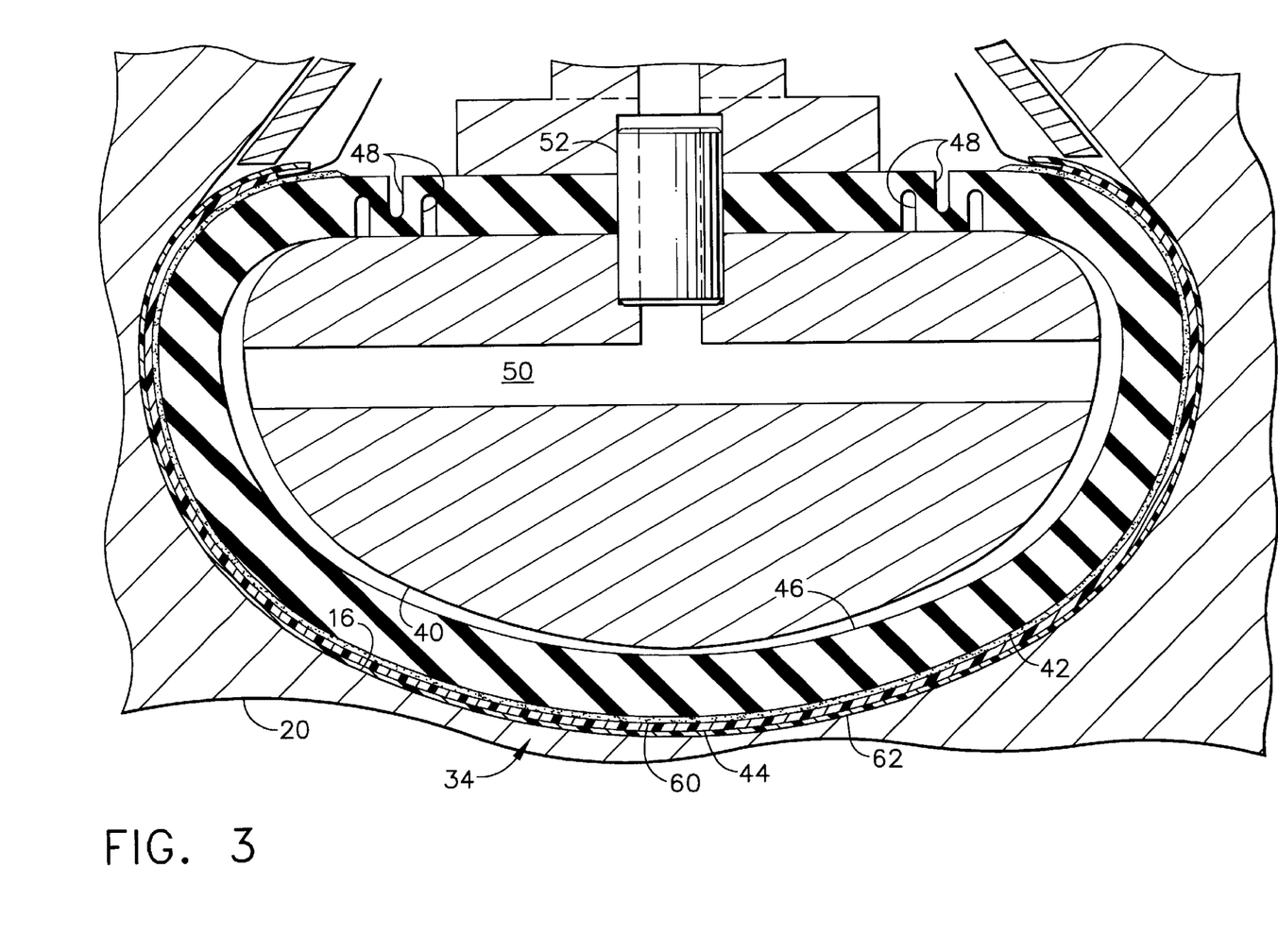
FIG. 3 is a detail similar to FIG. 2 showing the probe in an expanded position.

The probe 12 generally comprises a base 30, a support 32 extending downward from the base, and a head (generally designated by 34) mounted on an end of the support opposite the base. As illustrated in FIG. 2, the head 34 comprises a core 40, an expandable elastic element 42 and an eddy current array 44. Although the core 40 may be made of other materials without departing from the scope of the present invention, the core of the preferred embodiment is molded from semi-rigid polyurethane. The core 40 and the elastic element 42 define an interior space 46 (FIG. 3) which is expandable by introducing a pressurized fluid therein from a collapsed position as illustrated in FIG. 2 to an expanded position as illustrated in FIG. 3. When the interior space 46 is in the collapsed position the probe 12 is sized and shaped for inserting the probe into and removing the probe from the opening 18 in the component 20, and when the interior space is in the expanded position the probe is sized and shaped for at least partially filling the opening and for contacting the preselected surface 16 of the component to inspect the surface. Although the expandable element 42 may be made of other materials without departing from the scope of the present invention, the element of the preferred embodiment is made from polyurethane sheet. To avoid damaging the array 44, the expandable element 42 preferentially stretches outside the portion attached to the array and does not substantially stretch in the portion attached to the array. To improve the ease with which the element 42 expands and flexes outside the portion attached to the array 44, slots 48 are formed in the element.

Figure 4:
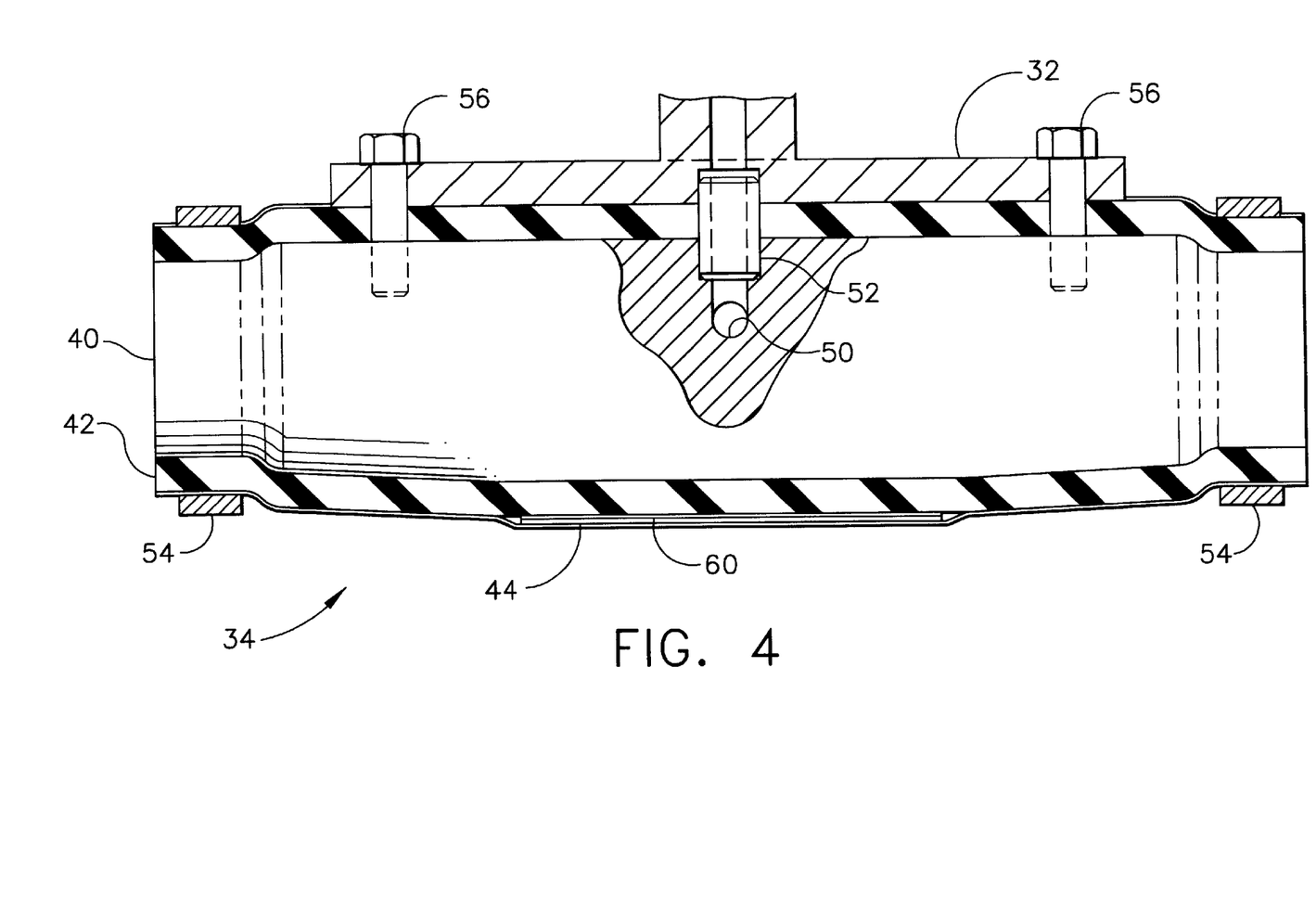
FIG. 4 is a cross section of the probe taken in the plane of line 4—4 of FIG. 2.

A T-shaped passage 50 extends through the core 40 to the interior space 46 for delivering fluid from the fluid delivery system 14 to the interior space. A threaded nipple 52 is provided at the inlet of the passage 50 for connecting the passage to the fluid delivery system 14. As illustrated in FIG. 4, clamps 54 are provided adjacent the longitudinal ends of the head 34 for attaching the expandable element 42 to the core 40 and for sealing the ends of the interior space 46. It is envisioned that the expandable element 42 may be sealingly attached to the core 40 along its upper surface to prevent pressurized fluid from leaking out of the probe 12. As further illustrated in FIG. 4, the head 34 is attached to the support 32 by bolts 56.

As shown in FIG. 2, the eddy current array 44 is bonded to an outer face of the expandable element 42 by an adhesive layer 60, and a protective covering 62 having a low coefficient of friction is adhesively bonded to the array 44 and the expandable element 42 to permit the probe 12 to easily slide across the preselected surface 16 of the component 20 as it is inserted in the opening 18 and removed from the opening. Although the covering 62 may be made of other materials without departing from the scope of the present invention, the covering of the preferred embodiment is Teflon7 polytetrafluoroethylene tape having a nominal thickness of about 0.0045 inches. Teflon7 is a federally registered trademark of E.I. du Pont de Nemours and Company of Wilmington, Del. As shown in FIG. 1, the eddy current array 44 is connected to a conventional eddy current instrument 64 for providing an output related to flaw size in the surface 16 of the component 20. The array 44, which is conventional, generates and detects magnetic fields in the component 20 to inspect the preselected surface 16 of the component. The eddy current array 44 has an outer surface shaped substantially identically to the preselected surface 16 of the component 20 when the expandable element 42 is in the expanded position.

As further illustrated in FIG. 1, the fluid delivery system 14 includes a reservoir 70 operatively connected to the interior space 46 by tubing 72 extending through the support 32 for introducing pressurized fluid to the interior space. In one embodiment, the reservoir 70 is filled with a liquid such as hydraulic fluid. In another embodiment, the reservoir 70 is filled with a gas such as air. The fluid may be driven from the reservoir 70 by any conventional means to pressurize the interior space 46 of the probe 12. For example, in a first embodiment the fluid is expelled from the reservoir 70 by a piston 74 driven by a piston rod 76. A valve 78 positioned along the tubing 72 permits the tubing to be blocked to prevent fluid from leaking out of the reservoir 70 when the probe 12 is removed.

Figure 5:
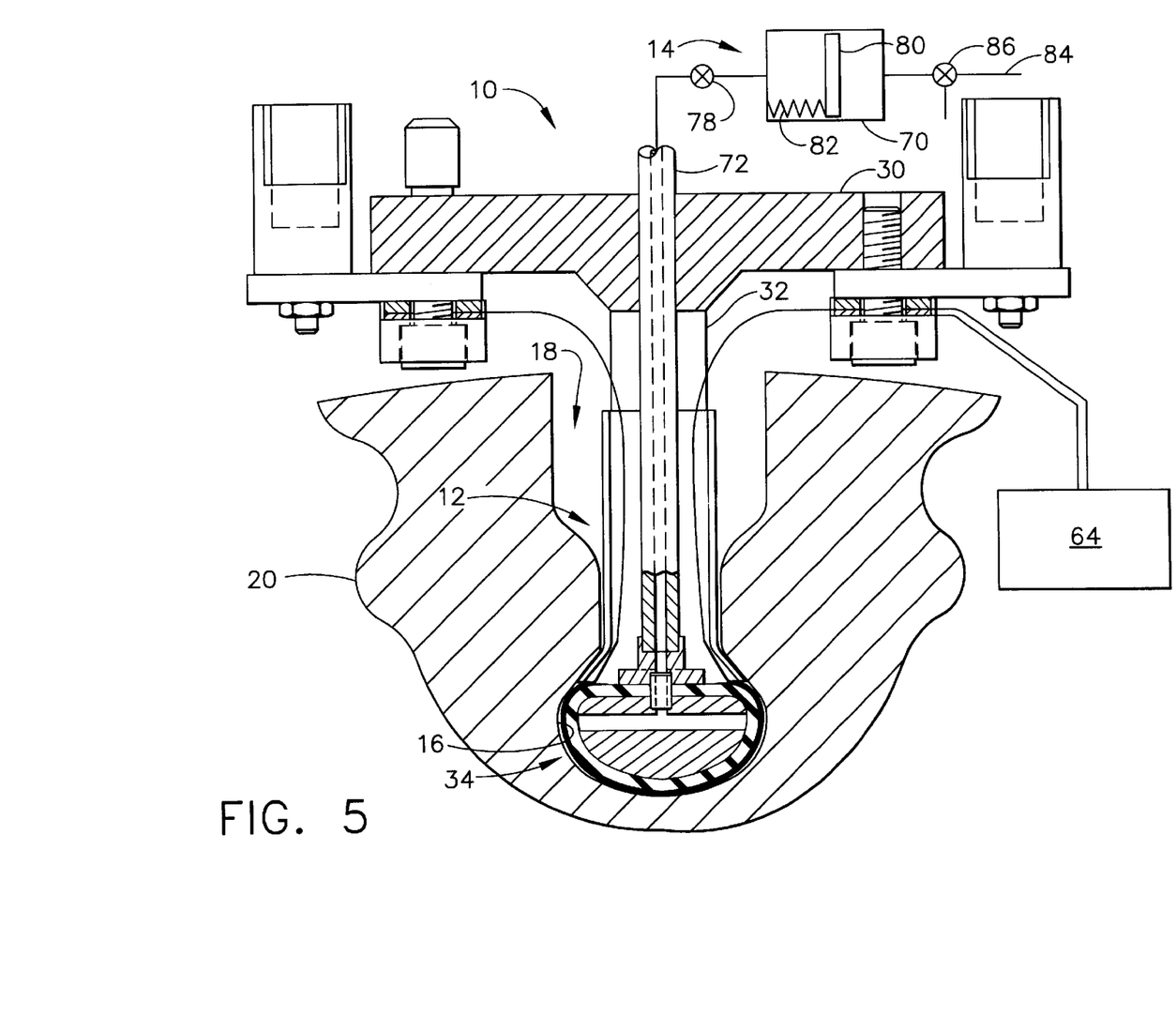
FIG. 5 is a vertical cross section of a second embodiment of an eddy current inspection system of the present invention.

In a second embodiment of the fluid delivery system 14 shown in FIG. 5, the fluid is expelled from the reservoir 70 by a piston 80 driven by a spring 82 and a second pressurized fluid. Although other first and second fluids may be used without departing from the scope of the present invention, in one embodiment the first fluid is hydraulic fluid and the second fluid is air provided by a shop air supply line 84. Although the spring 82 may be placed in other positions without departing from the scope of the present invention, in one embodiment the spring is positioned to drive the piston in a direction selected to expel fluid from the reservoir and introduce the fluid to the interior space 46 of the expandable element 42. A valve 86 positioned along the shop air supply line 84 directs pressurized fluid to the reservoir 70, and alternatively, vents fluid from the reservoir.

Figure 6:
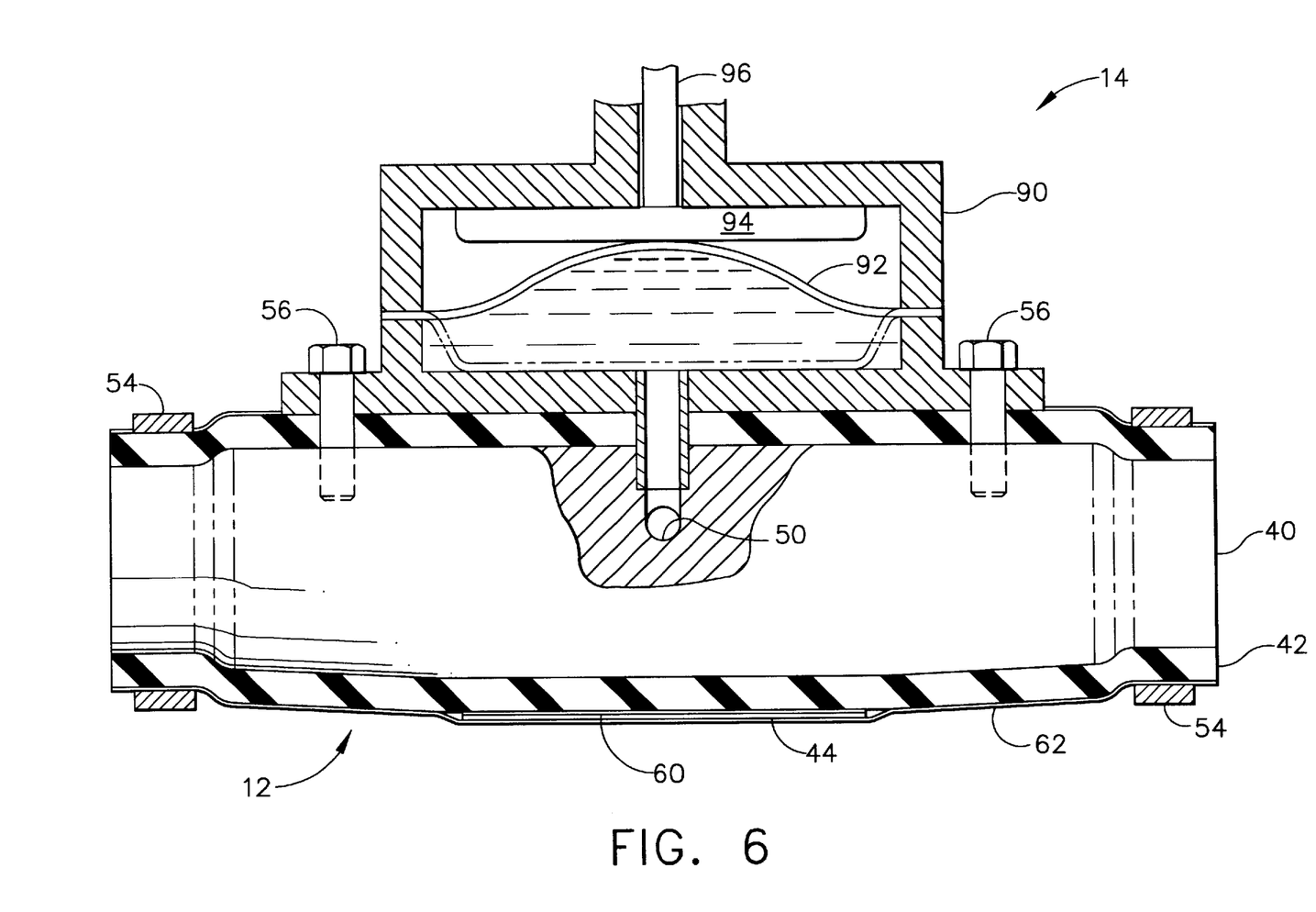
FIG. 6 is a vertical cross section of a third embodiment of the inspection system.

A third embodiment of the fluid delivery system 14 shown in FIG. 6 includes a fluid reservoir 90 inside the probe 12. A bladder 92 extending across the reservoir 90 may be displaced (downward as shown) to expel fluid from the reservoir through the passage 50 and into the interior space 46 of the probe 12. Any conventional means may be used to displace the bladder 92 to expel the fluid from the reservoir 90. For example, the fluid delivery system 14 may include a piston 94 driven by a piston rod 96 to displace the bladder 92.

To assemble the probe 12, the eddy current array 44 and covering 62 are bonded to the expandable element 42, and the covering and expandable element are clamped to the core 40. Preferably, the expandable element 42 is bonded to the core 40 everywhere except over the array 44. When assembled, the probe 12 may be used in a conventional manner.

Figure 7:
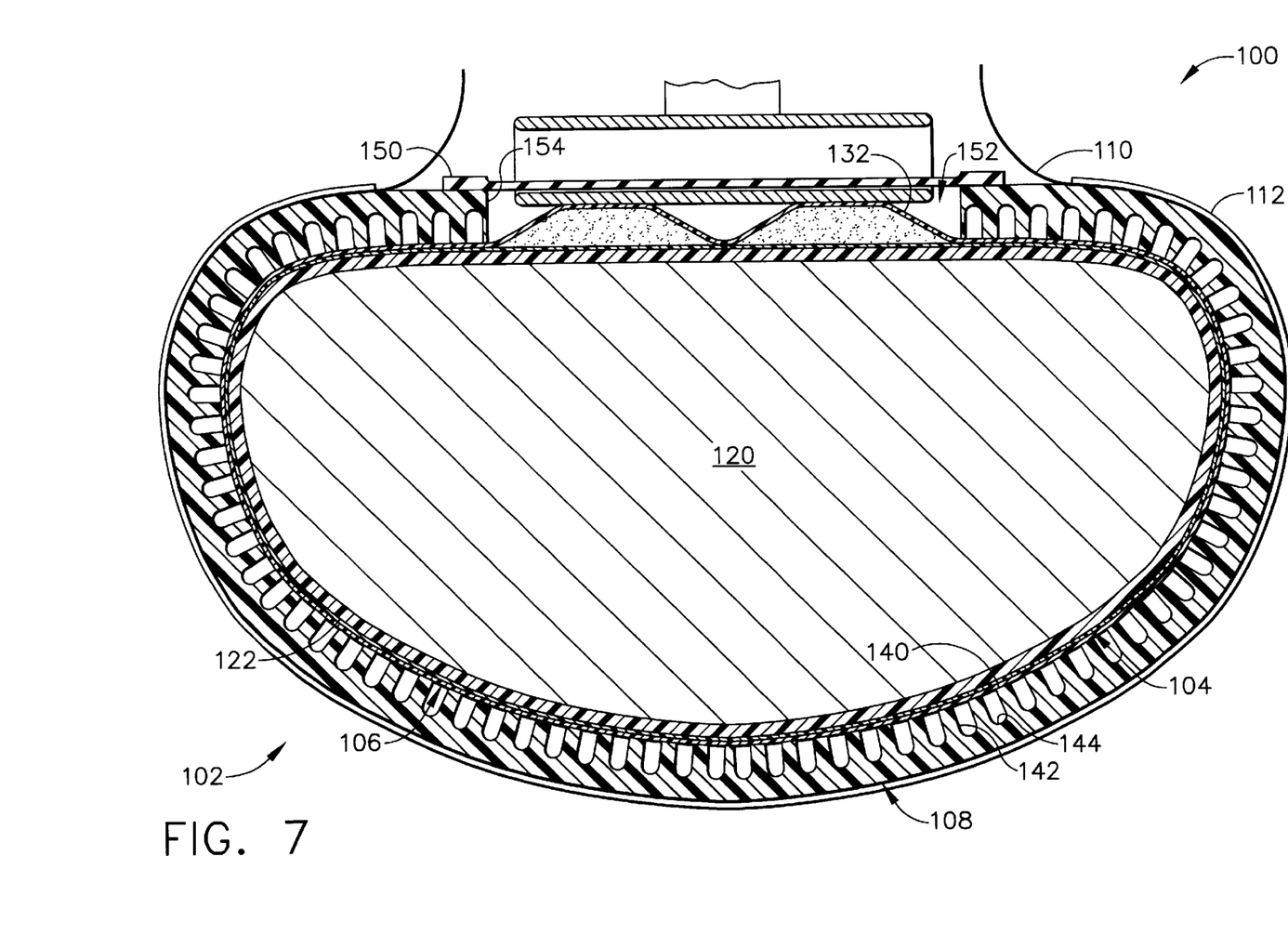
FIG. 7 is a detail showing an alternative probe configuration shown in a collapsed position.
Figure 8:
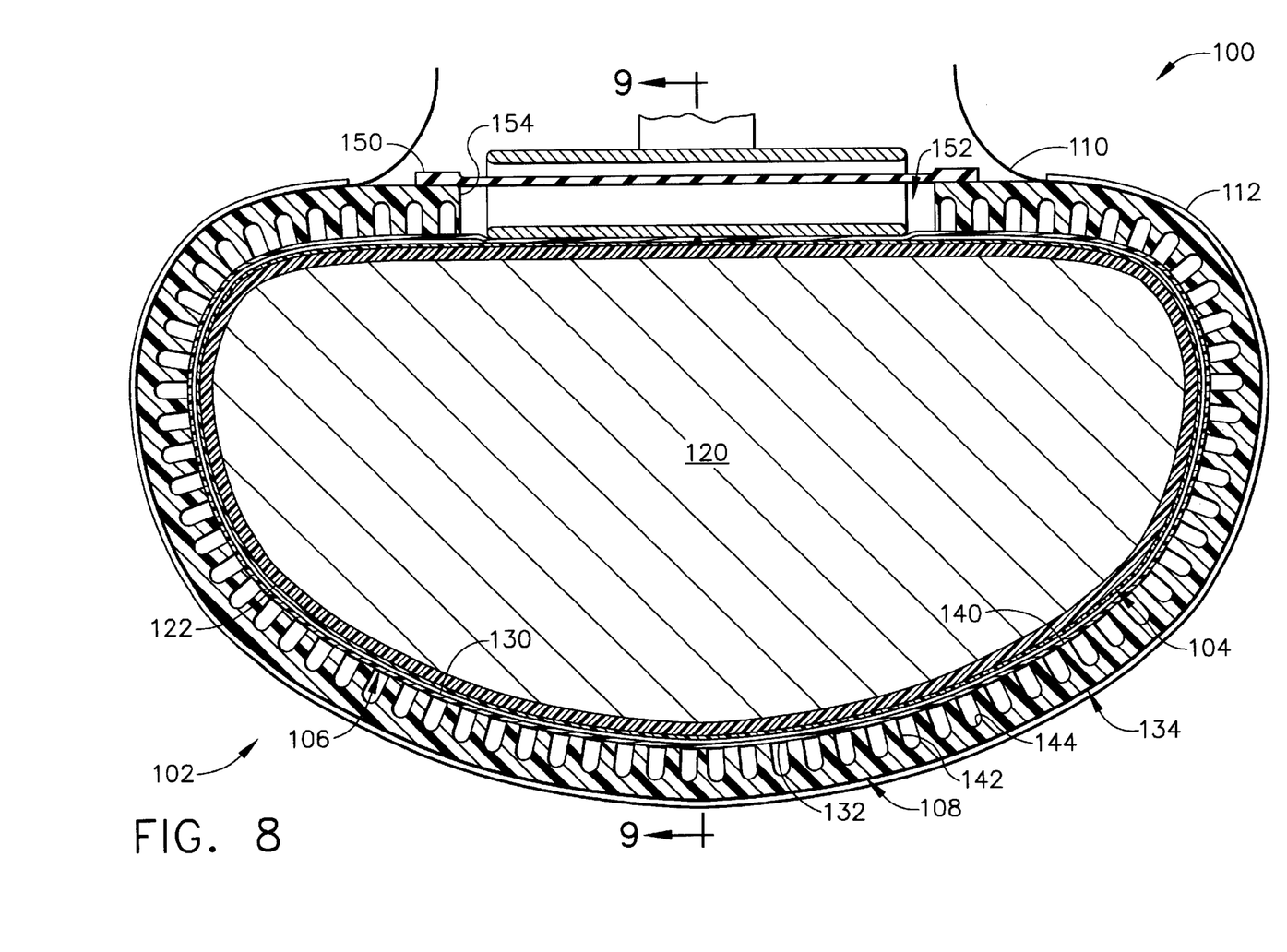
FIG. 8 is a detail similar to FIG. 7 showing the alternative probe configuration in an expanded position.
Figure 9:
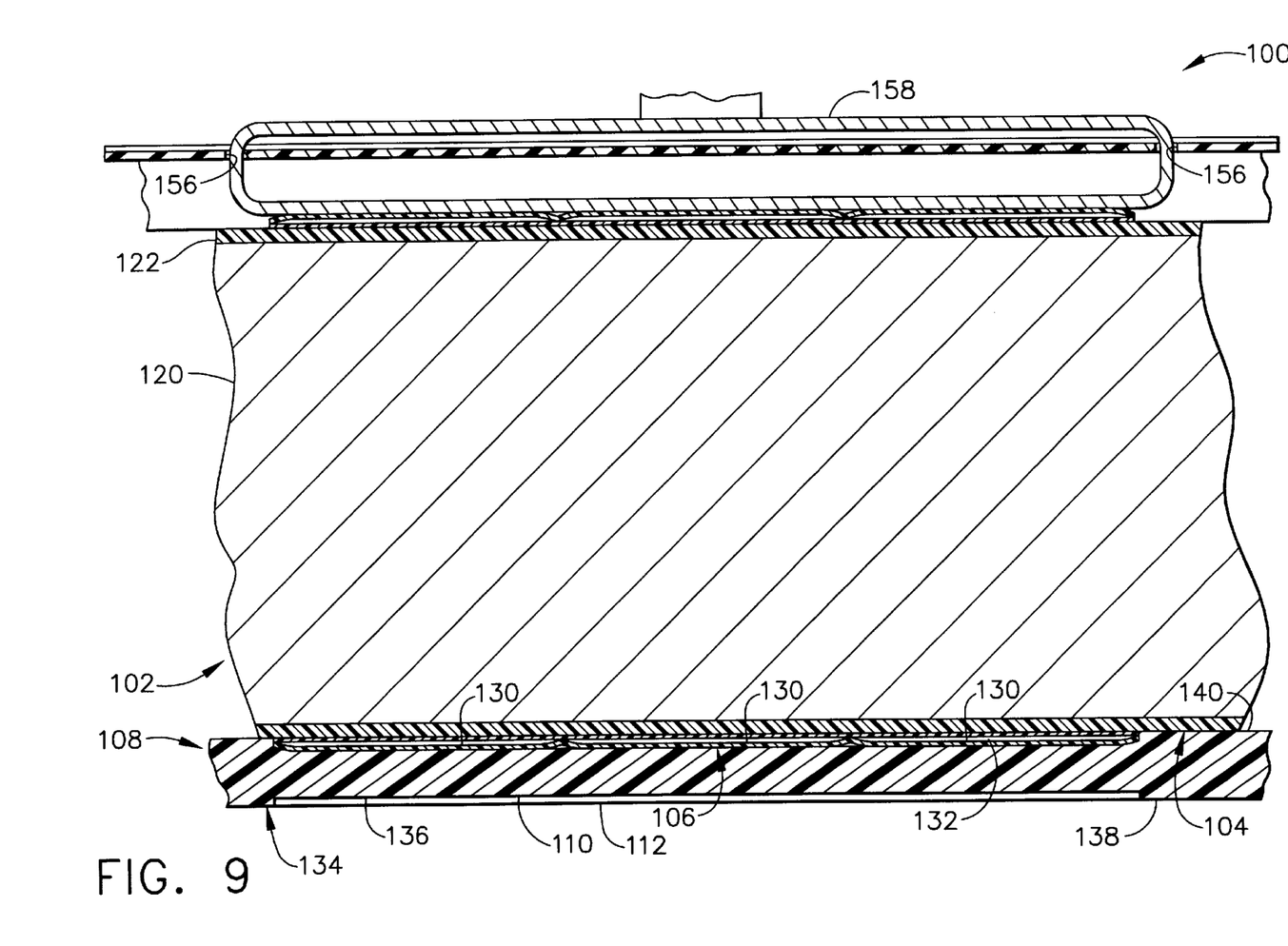
FIG. 9 is a cross section of the alternative probe configuration taken in the plane of line 9—9 of FIG. 8.

A probe of an alternative embodiment, generally designated by 100, is illustrated in FIGS. 7–9. The probe 100 is similar to the probe 12 of the first embodiment except for its head, generally designated by 102. As illustrated in FIG. 7, the head 102 of the alternative embodiment comprises a core (generally designated by 104), an expandable elastic element (generally designated by 106), a covering (generally designated by 108), a conventional eddy current array 110, and a protective sheet 112 covering the array. The core 104 includes a solid inner body 120 wrapped with one or more layers of shaping material 122 to provide the desired size and shape. Although the body 120 may be made of other materials without departing from the scope of the present invention, in one embodiment the body is molded from semi-rigid polyurethane. Although the shaping material 122 may be other materials without departing from the scope of the present invention, in one embodiment the material is Kapton7 tape. Kapton7 is a federally registered trademark of E.I. du Pont de Nemours and Company.

The expandable elastic element 106 is a bladder having one or more chambers 130 (FIGS. 8 and 9) formed therein. Although the bladder may have fewer or more chambers 130 without departing from the scope of the present invention, in one embodiment the bladder has three chambers 130 and the eddy current array 110 is positioned over the central chamber 130 of the bladder. Although the bladder may be made of other materials without departing from the scope of the present invention, in one embodiment the bladder is constructed of a thermally or ultrasonically weldable polyethylene so the chambers 130 can be formed by thermal or ultrasonic welding. Each of the chambers 130 is filled with a fluid 132. Although other fluids may be used without departing from the scope of the present invention, in one embodiment the fluid is a non-conducting liquid. Preferably, the material used to form the bladder is flexible, fatigue resistant, easily and permanently sealable, resistant to degradation by the fluid 132 used to expand it and bondable to both the shaping material 122 and the covering 108. Although the expandable element 106 may attached to the core 104 in other ways without departing from the scope of the present invention, in one embodiment the element is adhesively bonded to the core.

The covering 108 positioned over the expandable elastic element 106 has an outer face, generally designated by 134, having a recessed central portion 136 and opposite end portions 138 extending longitudinally outward from the central portion. In one embodiment, the covering 108 is adhesively bonded to the expandable element 106. As illustrated in FIG. 9, the recessed central portion 136 of the outer face 134 receives the eddy current array 110. The array 110 is adhesively bonded to the central portion 136 of the covering. As illustrated in FIGS. 7 and 8, an inner face 140 of the covering 108 opposite the outer face 132 has longitudinal ribs 142 separated by longitudinal slots 144 which give the covering flexibility. Although the covering 108 may be made of other materials without departing from the scope of the present invention, in one embodiment the covering is a molded polyurethane.

An elastic band 150 is attached to the covering 108 across an opening, generally designated by 152, formed between its lateral ends 154. Slots 156 (FIG. 9) extending through the band 150 provide access for a mechanical actuator 158 which is configured to drive the expandable elastic element 106 from the collapsed configuration shown in FIG. 7 to the expanded configuration shown in FIG. 8 as it moves downward. The elastic band 150 returns the element 106 to the collapsed configuration from the expanded when the actuator 158 is moved upward. It is envisioned that the elastic band 150 may be omitted if the elastic element 106 has sufficient resiliency to return to its collapsed configuration without the band when the actuator 158 moves upward. Further, it is envisioned that the elastic band 150 may be omitted if an external reservoir capable of pumping the fluid 132 out of the bladder is used to return it to the collapsed configuration. As will be appreciated by those skilled in the art, a lower portion of each chamber 130 of the elastic element 106 of the alternative embodiment of the probe 100 defines an expandable interior space and an upper portion of each chamber defines a reservoir operatively connected to the interior space for selectively expanding and collapsing the probe.

The protective sheet 112 is adhesively bonded to the outer surface of the array 110. Preferably, the sheet 112 has a low coefficient of friction to permit the probe 110 to easily slide across the preselected surface 16 of the component 20 as it is inserted in the opening 18 and removed from the opening. Although the sheet 112 may be made of other materials without departing from the scope of the present invention, the sheet of the preferred embodiment is Teflon7.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An eddy current inspection probe for inspecting a preselected surface at least partially defining an opening in a component, said eddy current inspection probe comprising:

an expandable element at least partially defining an interior space which is expandable by introducing a pressurized fluid into the interior space from a collapsed position for inserting the probe into and removing the probe from the opening in the component to an expanded position in which the probe is sized and shaped for at least partially filling the opening and for contacting the preselected surface of the component for inspecting the surface; and an eddy current array positioned over the expandable element for generating and detecting magnetic fields in the component to inspect the preselected surface of the component, the eddy current array having an outer surface shaped substantially identically to the preselected surface of the component when the expandable element is in the expanded position for maintaining the outer surface of the array at a preselected distance from the surface of the component.

2. A probe as set forth in claim 1 further comprising a core having an exterior surface sized and shaped for receipt within the opening of the component, the expandable element being positioned over the exterior surface of the core.

3. A probe as set forth in claim 1 in combination with a fluid delivery system comprising a reservoir operatively connected to the interior space of the expandable element for introducing pressurized fluid to the interior space.

4. A probe as set forth in claim 3 wherein the reservoir is filled with liquid.

5. A probe as set forth in claim 4 wherein the reservoir is filled with hydraulic fluid.

6. A probe as set forth in claim 3 wherein the reservoir is filled with gas.

7. A probe as set forth in claim 6 wherein the reservoir is filled with air.

8. A probe as set forth in claim 3 further comprising a bladder extending across the reservoir, said bladder being moveable to expel fluid from the reservoir and into the interior space of the expandable element.

9. A probe as set forth in claim 8 wherein the fluid delivery system includes a piston for moving the bladder to expel fluid from the reservoir.

10. A probe as set forth in claim 3 wherein the fluid delivery system includes a piston mounted inside the reservoir for expelling fluid from the reservoir and introducing the fluid to the interior space of the expandable element.

11. A probe as set forth in claim 10 wherein the piston is mechanically driven.

12. A probe as set forth in claim 10 wherein the piston is pneumatically driven.

13. A probe as set forth in claim 12 wherein the fluid delivery system includes a spring attached to the piston.

14. A probe as set forth in claim 13 wherein the spring is positioned to drive the piston to expel fluid from the reservoir and introduce the fluid to the interior space of the expandable element.

15. A probe as set forth in claim 3, wherein the expandable element defines both the interior space and the reservoir.

* * * * *